(12) United States Patent
Herfert et al.

(10) Patent No.: US 10,226,753 B2
(45) Date of Patent: Mar. 12, 2019

(54) PROCESS FOR PRODUCING SUPERABSORBENTS

(71) Applicant: BASF SE, Ludwigshafen am Rhein (DE)

(72) Inventors: Norbert Herfert, Shanghai (CN); Wanthip Poomsuwan, Chon Buri (TH); Thomas Gieger, Ludwigshafen (DE)

(73) Assignees: BASF SE, Ludwigshafen (DE); BASF (THAI) LTD., Bangkok (TH)

( * ) Notice: Subject to any disclaimer, the term of this patent is extended or adjusted under 35 U.S.C. 154(b) by 0 days.

(21) Appl. No.: 15/746,492

(22) PCT Filed: Jul. 21, 2016

(86) PCT No.: PCT/EP2016/067411
§ 371 (c)(1),
(2) Date: Jan. 22, 2018

(87) PCT Pub. No.: WO2017/021167
PCT Pub. Date: Feb. 9, 2017

(65) Prior Publication Data
US 2018/0200691 A1    Jul. 19, 2018

(30) Foreign Application Priority Data
Aug. 5, 2015    (EP) ..................................... 15179835

(51) Int. Cl.
| | |
|---|---|
| B01J 20/26 | (2006.01) |
| A61L 15/60 | (2006.01) |
| C08F 2/01 | (2006.01) |
| C08F 2/10 | (2006.01) |
| C08F 220/06 | (2006.01) |
| C09D 183/08 | (2006.01) |
| C08J 3/12 | (2006.01) |
| C08L 33/02 | (2006.01) |
| A61L 15/22 | (2006.01) |
| B01J 19/06 | (2006.01) |
| B01J 20/30 | (2006.01) |
| C08J 3/24 | (2006.01) |
| C08G 77/28 | (2006.01) |

(52) U.S. Cl.
CPC ........... *B01J 20/267* (2013.01); *A61L 15/225* (2013.01); *A61L 15/60* (2013.01); *B01J 19/06* (2013.01); *B01J 20/261* (2013.01); *B01J 20/3085* (2013.01); *C08F 2/01* (2013.01); *C08F 2/10* (2013.01); *C08F 220/06* (2013.01); *C08J 3/12* (2013.01); *C08J 3/247* (2013.01); *C09D 183/08* (2013.01); *B01J 2219/0015* (2013.01); *B01J 2219/00076* (2013.01); *C08G 77/28* (2013.01); *C08J 2333/02* (2013.01); *C08L 33/02* (2013.01)

(58) Field of Classification Search
CPC .... B01J 20/267; B01J 20/261; B01J 20/3085; B01J 19/06; B01J 2219/00076; B01J 2219/0015; C08F 2/01; C08F 2/10; C08F 220/06; A61L 15/60; A61L 15/225; C08J 3/12; C08J 3/247; C08J 2333/02
USPC .............................................. 526/317, 317.1
See application file for complete search history.

(56) References Cited

U.S. PATENT DOCUMENTS

| | | | | |
|---|---|---|---|---|
| 5,210,298 | A * | 5/1993 | Shimomura | ............ C07C 51/50 526/240 |
| 5,338,810 | A * | 8/1994 | Shimomura | ............ C07C 51/50 526/240 |
| 2010/0056739 | A1* | 3/2010 | Funk | ..................... C07C 51/412 526/317.1 |

FOREIGN PATENT DOCUMENTS

| | | |
|---|---|---|
| EP | 0 372 706 A2 | 6/1990 |
| WO | WO-2008/116840 A1 | 10/2008 |
| WO | WO-2008116840 A1 * | 10/2008 ........... C07C 51/412 |
| WO | WO-2012/163930 A1 | 12/2012 |

OTHER PUBLICATIONS

Buchholz, F., et al., eds., "Modern Superabsorbent Polymer Technology," Wiley-VCH, NY, NY (1998), pp. 71-103.
International Search Report for PCT Patent Application No. PCT/EP2016/067411, dated Oct. 4, 2016.

* cited by examiner

*Primary Examiner* — Michael Bernshteyn
(74) *Attorney, Agent, or Firm* — Marshall, Gerstein & Borun LLP

(57) ABSTRACT

The invention relates to a process for producing superabsorbents, comprising the preparation of partly neutralized acrylic acid by the steps (i) preparing an over-neutralized acrylic acid having a degree of neutralization of at least 100.1 mol-% by mixing of an acrylic acid 1 and a base and (ii) preparing a neutralized acrylic acid having a degree of neutralization from 50 to 85 mol-% by mixing of the over-neutralized acrylic acid and an acrylic acid 2, wherein the content of dimeric acrylic acid in the acrylic acid 2 is lower than the content of dimeric acrylic acid in the acrylic acid 1.

12 Claims, No Drawings

PROCESS FOR PRODUCING SUPERABSORBENTS

CROSS-REFERENCE TO RELATED APPLICATIONS

This application is the U.S. National Stage application of International Patent Application No. PCT/EP2016/067411, filed Jul. 21, 2016, which claims the benefit of European Patent Application No. 15179835.2, filed Aug. 5, 2015.

The invention relates to a process for producing superabsorbents, comprising the preparation of partly neutralized acrylic acid by the steps (i) preparing an over-neutralized acrylic acid having a degree of neutralization of at least 100.1 mol-% by mixing of an acrylic acid 1 and a base and (ii) preparing a neutralized acrylic acid having a degree of neutralization from 50 to 85 mol-% by mixing of the over-neutralized acrylic acid and an acrylic acid 2, wherein the content of dimeric acrylic acid in the acrylic acid 2 is lower than the content of dimeric acrylic acid in the acrylic acid 1.

Superabsorbents are used to produce diapers, tampons, sanitary napkins and other hygiene articles, but also as water-retaining agents in market gardening. The superabsorbents are often also referred to as "absorbent resins", "superabsorbents", "superabsorbent polymers", "absorbent polymers", "absorbent gelling materials", "hydrophilic polymers" or "hydrogels".

The production of superabsorbents is described in the monograph "Modern Superabsorbent Polymer Technology", F. L. Buchholz and A. T. Graham, Wiley-VCH, 1998, pages 71 to 103.

EP 0 372 706 A2 teaches a process for producing superabsorbents comprising a multi-step neutralization process for acrylic acid. Using the multi-step neutralization process reduces the amount of residual monomers in the formed superabsorbents.

WO 2012/163930 A1 discloses a process for producing superabsorbents comprising the use of acrylic acid having a high content of dimeric acrylic acid.

It was an object of the present invention to provide a process for producing superabsorbents having a constant low level of residual monomers.

The object was achieved by a process for producing superabsorbents, comprising polymerization of a monomer solution, comprising
  a) partly neutralized acrylic acid,
  b) at least one crosslinker,
  c) at least one initiator,
  d) optionally one or more ethylenically unsaturated monomers copolymerizable with the acrylic acid mentioned under a) and
  e) optionally one or more water-soluble polymers,
drying, grinding and classifying the resulting polymer gel, optionally thermally postcrosslinking and cooling the resulting polymer particles, wherein the partly neutralized acrylic acid was prepared in a process, comprising
  i) preparing an over-neutralized acrylic acid having a degree of neutralization of at least 100.1 mol-% by mixing an acrylic acid 1 and a base and
  ii) preparing a neutralized acrylic acid having a degree of neutralization from 50 to 85 mol-% by mixing the over-neutralized acrylic acid and an acrylic acid 2, wherein the content of dimeric acrylic acid in the acrylic acid 2 is lower than the content of dimeric acrylic acid in the acrylic acid 1.

The content of dimeric acrylic acid is determined by liquid chromatography with ultraviolet detection.

The content of dimeric acrylic acid in the acrylic acid 2 is preferably at least 0.1% by weight, more preferably at least 0.25% by weight, most preferably at least 0.4% by weight, lower than the content of dimeric acrylic acid in the acrylic acid 1.

The content of dimeric acrylic acid in the acrylic acid 1 is preferably at least 0.2% by weight, more preferably at least 0.35% by weight, most preferably at least 0.5% by weight.

The content of dimeric acrylic acid in the acrylic acid 2 is preferably less than 0.5% by weight, more preferably less than 0.35% by weight, most preferably less than 0.2% by weight.

The degree of neutralization of the over-neutralized acrylic acid is preferably from 100.5 to 108 mol-%, more preferably from 101 to 106 mol-%, most preferably from 101.5 to 104 mol-%.

In a preferred embodiment of the present invention, the base is aqueous sodium hydroxide and/or aqueous potassium hydroxide.

The present invention bases on the finding that the degree of neutralization of the over-neutralized acrylic acid and the dosing sequence of the two different acrylic acids have a strong impact on the amount of residual monomer in the formed superabsorbent.

In a preferred embodiment of the present invention, the temperature of the acrylic acid 1 and/or the temperature of the acrylic acid 2 is in the range from 15 to 25° C.

In a preferred embodiment of the present invention, acrylic acid having a lower content of dimeric acrylic acid than the acrylic acid 2 is used as new acrylic acid 2 and the former acrylic acid 2 is combined with the former acrylic acid 1 forming new acrylic acid 1. That means that on delivery of acrylic acid having a low content of dimeric acrylic, the content of the tank for storing acrylic acid 2 is transferred into the tank for storing acrylic acid 1, and the newly delivered acrylic acid having a low content of dimeric acrylic acid is transferred in the tank for storing acrylic acid 2.

The present invention further provides an apparatus for production of superabsorbents, comprising at least two tanks for acrylic acid, wherein the at least two tanks for acrylic acid are each connected with a means for neutralization, and the at least two tanks for acrylic acid are interconnected so that the content of one tank for acrylic acid can be discharged into the other tank for acrylic acid.

In a preferred embodiment of the present invention, the tanks for acrylic acid have each an internal recycling line comprising a pump and a heat exchanger.

In a preferred embodiment of the present invention, the tanks for acrylic acid are thermal insulated.

By the use of the internal recycling line and/or the thermal insulation the temperature of acrylic acid can be kept in the preferred range.

The production of the superabsorbents is described in detail hereinafter:

The superabsorbents are produced by polymerizing a monomer solution, and are typically water-insoluble.

Acrylic acid typically comprises polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on unneutralized acrylic acid. For example, the monomer solution can be prepared by using acrylic acid with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of acrylic acid. In addition, polyvalent metal salts which can form coordinate bonds with at least two acid groups of acrylic acid are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight and most preferably 0.3 to 0.6% by weight, based in each case on unneutralized acrylic acid. With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. However, the reducing component used is preferably disodium 2-hydroxy-2-sulfonatoacetate or a mixture of disodium 2-hydroxy-2-sulfinatoacetate, disodium 2-hydroxy-2-sulfonatoacetate and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with acrylic acid are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

For better control of the polymerization reaction, it is optionally possible to add all known chelating agents to the monomer solution or suspension or to the raw materials thereof. Suitable chelating agents are, for example, phosphoric acid, diphosphoric acid, triphosphoric acid, polyphosphoric acid, citric acid, tartaric acid, or salts thereof.

Further suitable examples are iminodiacetic acid, hydroxyethyliminodiacetic acid, nitrilotriacetic acid, nitrilotripropionic acid, ethylenediaminetetraacetic acid, diethylenetriaminepentaacetic acid, triethylenetetraaminehexaacetic acid, N,N-bis(2-hydroxyethyl)glycine and trans-1,2-diaminocyclohexanetetraacetic acid, and salts thereof. The amount used is typically 1 to 30 000 ppm based on the monomers a), preferably 10 to 1000 ppm, preferentially 20 to 600 ppm, more preferably 50 to 400 ppm, most preferably 100 to 300 ppm.

The monomer solution is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 50 to 85 mol %, more preferably from 60 to 80 mol % and most preferably from 65 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, potassium hydroxide and also mixtures thereof.

The resulting polymer gel is dried. The driers are not subject to any restriction. However, the drying of the polymer gel is preferably performed with a belt drier until the residual moisture content is preferably 0.5 to 10% by weight, more preferably 1 to 7% by weight and most preferably 2 to 5% by weight, the residual moisture content being determined by EDANA recommended test method No. WSP 230.2(05) "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent grinding steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Subsequently, the dried polymer gel is ground and classified. The apparatus used for grinding may typically be single- or multistage roll mills, preferably two- or three-stage roll mills, pin mills, hammer mills or vibratory mills.

The mean particle size of the polymer particles removed as the product fraction is preferably at least 200 μm, more preferably from 250 to 600 μm and very particularly from 300 to 500 μm. The mean particle size of the product fraction may be determined by means of EDANA recommended test method No. WSP 220.2(05) "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 μm is preferably at least 90% by weight, more preferably at least 95% by weight, most preferably at least 98% by weight.

Polymer particles with too small a particle size lower the saline flow conductivity (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting superabsorbents. However, this can be compensated for, for example, by adjusting the amount of crosslinker b) used.

When the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

The proportion of particles having a particle size of at most 600 μm is preferably at least 90% by weight, more preferably at least 95% by weight, most preferably at least 98% by weight.

Polymer particles of excessively large particle size lower the free swell rate (FSR). The proportion of excessively large polymer particles should therefore likewise be small.

Excessively large polymer particles are therefore typically removed and recycled into the grinding of the dried polymer gel.

To improve the properties, the polymer particles may subsequently be thermally surface postcrosslinked. Suitable surface postcrosslinkers are compounds which comprise groups which can form covalent bonds with at least two acid groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and derivatives thereof in WO 2003/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal surface postcrosslinking is preferably performed in contact driers, more preferably paddle driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany) and Nara Paddle Dryer (NARA Machinery Europe; Frechen; Germany). Moreover, fluidized bed driers may also be used.

The thermal surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred surface postcrosslinking temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the superabsorbents tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the saline flow conductivity (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The superabsorbents produced by the process according to the invention have a centrifuge retention capacity (CRC) of typically at least 15 g/g, preferably at least 20 g/g, more preferably at least 22 g/g, especially preferably at least 24 g/g and most preferably at least 26 g/g. The centrifuge retention capacity (CRC) of the superabsorbents is typically less than 60 g/g. The centrifuge retention capacity (CRC) is determined by EDANA recommended test method No. WSP 241.2(05) "Gravimetric Determination of Fluid Retention Capacity in Saline Solution After Centrifugation".

The superabsorbents produced by the process according to the invention have an absorption under high load (AUHL) of typically at least 15 g/g, preferably at least 20 g/g, more preferably at least 22 g/g, especially preferably at least 24 g/g and most preferably at least 26 g/g. The absorption under high load (AUHL) of the superabsorbents is typically less than 35 g/g. The absorption under high load (AUHL) is determined analogously to EDANA recommended test method No. WSP 242.2(05) "Gravimetric Determination of Absorption Under Pressure", except that a pressure of 49.2 $g/cm^2$ is established instead of a pressure of 21.0 $g/cm^2$.

Methods:

The measurements should, unless stated otherwise, be carried out at an ambient temperature of 23±2° C. and a relative atmospheric humidity of 50±10%. The water-absorbent polymers are mixed thoroughly before the measurement.

Residual Monomers

The residual monomers in superabsorbents are determined by EDANA recommended test method No. WSP 210.2(04) "Residual Monomers".

Centrifuge Retention Capacity (CRC)

The centrifuge retention capacity of superabsorbents is determined by the EDANA recommended test method No. WSP 241.2(05) "Gravimetric Determination of Fluid Retention Capacity in Saline Solution After Centrifugation", wherein for higher values of the centrifuge retention capacity lager tea bags have to be used.

Absorbency Under High Load (AUHL)

The absorbency under high load of superabsorbents is determined analogously to the EDANA recommended test method No. WSP 242.2(05) "Gravimetric Determination of Absorption Under Pressure", except using a weight of 49.2 g/cm$^2$ instead of a weight of 21.0 g/cm$^2$.

Extractables

The content of extractable constituents in superabsorbents is determined by the EDANA recommended test method No. WSP 270.2(05) "Determination of Extractable Polymer Content by Potentiometric Titration".

Free Swell Rate (FSR)

1.00 g (=W1) of the dry water-absorbent polymer particles is weighed into a 25 ml glass beaker and is uniformly distributed on the base of the glass beaker. 20 ml of a 0.9% by weight sodium chloride solution are then dispensed into a second glass beaker, the content of this beaker is rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

$$FSR\ [g/gs] = W2/(W1 \times t)$$

When the moisture content of the hydrogel-forming polymer is more than 3% by weight, however, the weight W1 must be corrected for this moisture content.

Saline Flow Conductivity (SFC)

The saline flow conductivity of a swollen gel layer under a pressure of 0.3 psi (2070 Pa) is determined, as described in EP 2 535 698 A1, with a weight of 1.5 g of water-absorbing polymer particles as a urine permeability measurement (UPM) of a swollen gel layer. The flow is detected automatically.

The saline flow conductivity (SFC) is calculated as follows:

$$SFC\ [cm^3 s/g] = (Fg(t=0) \times L_0)/(d \times A \times WP)$$

where Fg(t=0) is the flow of NaCl solution in g/s, which is obtained using linear regression analysis of the Fg(t) data of the flow determinations by extrapolation to t=0, $L_0$ is the thickness of the gel layer in cm, d is the density of the NaCl solution in g/cm$^3$, A is the area of the gel layer in cm$^2$, and WP is the hydrostatic pressure over the gel layer in dynes/cm$^2$.

EXAMPLES

Example 1 (Inventive)

A 2 L stainless steel vessel was initially charged with 391.1 g of 50% by weight sodium hydroxide solution and 767.6 g of deionized water. The mixture was cooled down to 15° C. by means of a cooling bath. Then 320.6 g of initially part of acrylic acid having a content of dimeric acrylic acid of 6659 ppm (acrylic acid 1) were added while stirring. The rate of addition was adjusted in such way that the temperature did not exceed 30° C. After addition, the mixture was kept at approximately 30° C. for 2 minutes. The degree of neutralization was 110 mol-%. The content of dimeric acrylic acid in the monomer solution was 0 ppm, based on acrylic acid. Thereafter, additional 149.6 g of second part of acrylic acid having a content of dimeric acrylic acid of 1973 ppm (acrylic acid 2) were added within approximately 15 minutes under stirring keeping the temperature of the mixture below 30° C. The degree of neutralization was 75 mol-%. The content of dimeric acrylic acid in the monomer solution was 344 ppm, based on acrylic acid. After addition of the second portion of acrylic acid, the mixture was cooled down to 20° C. and 1.32 g of Laromer 9015 X (ethoxylated trimethylolpropane triacrylate; available from BASF SE, Ludwigshafen, Germany) were added under stirring. Then 0.022 g of Irgacure® 651 and 0.044 g of Irgacure® 1173 were added under stirring and the mixture was cooled down to 15° C. The mixture was freed of oxygen by passing nitrogen through via a glass frit while cooling down the mixture to −0.5° C. Then the monomer solution was transferred to a glass dish. The dimensions of the glass dish were such that a layer thickness of the monomer solution of 7 cm was established. Then 7.42 g of an aqueous solution of sodium persulfate with strength of 10 wt.-% and 7.05 g of an aqueous solution of hydrogen peroxide with strength of 1 wt.-% were added and the monomer solution was stirred briefly with the aid of a glass rod. Finally, 5.64 g of an aqueous solution of Bruggolite® FF6 (mixture of the disodium salt of 2-hydroxy-2-sulfinatoacetic acid, the disodium salt of 2-hydroxy-2-sulonatoacetic acid, and sodium bisulfite; available from L. Brueggemann K G, Heilbronn, Germany) with strength of 1 wt.-% was added to the monomer solution under stirring with the glass rod and the mixture polymerized by placing the glass dish with the monomer solution under a UV lamp (UV intensity=25 mW/cm$^2$) for 16 minutes. The resulting gel was ground with the aid of a commercial meat grinder (Scharfen Meat Mincer model X70G) with a 6 mm perforated disk. 5.64 g of an aqueous solution of sodium bisulfite with strength of 5 wt.-% was sprayed onto the ground gel and the gel was passed through the meat grinder two more times. The resulting gel was dried in a laboratory drying cabinet at 175° C. for 60 minutes. The product was then ground by means of an ultra-centrifugal mill (Retsch model ZM100 with 12-tooth rotor and 1.5 mm ring sieve; speed at 14000 rpm) and the sieve fraction of 150 to 600 μm was obtained by sieving of the milled product.

The resulting polymer particles had a centrifuge retention capacity (CRC) of 42.8 g/g, an content of extractables of 15.4 wt. %, and a content of residual monomers of 485 ppm.

Example 2 (Inventive)

A 2 L stainless steel vessel was initially charged with 391.1 g of 50% by weight sodium hydroxide solution and 767.6 g of deionized water. The mixture was cooled down to 15° C. by means of a cooling bath. Then 345.8 g of initially part of acrylic acid having a content of dimeric acrylic acid of 6659 ppm (acrylic acid 1) were added while stirring. The rate of addition was adjusted in such way that the temperature did not exceed 30° C. After addition, the mixture was kept at approximately 30° C. for 2 minutes. The degree of neutralization was 102 mol-%. The content of dimeric acrylic acid in the monomer solution was 0 ppm, based on acrylic acid. Thereafter, additional 124.5 g of second part of acrylic acid having a content of dimeric acrylic acid of 1973 ppm (acrylic acid 2) were added within approximately 15 minutes under stirring keeping the temperature of the mixture below 30° C. The degree of neutralization was 75 mol-%. The content of dimeric acrylic acid in the monomer solution was 235 ppm, based on acrylic acid. After addition of the second portion of acrylic acid, the mixture was cooled down to 20° C. and 1.32 g of Laromer 9015 X (ethoxylated trimethylolpropane triacrylate; available from BASF SE, Ludwigshafen, Germany) were added under stirring. Then 0.022 g of Irgacure® 651 and 0.044 g of Irgacure® 1173 were added under stirring and the mixture was cooled down to 15° C. The mixture was freed of oxygen by passing nitrogen through via a glass frit while cooling down the mixture to −0.5° C. Then the monomer solution was transferred to a glass dish. The dimensions of the glass dish were such that a layer thickness of the monomer solution of 7 cm was established. Then 7.42 g of an aqueous solution of sodium persulfate with strength of 10 wt.-% and 7.05 g of an aqueous solution of hydrogen peroxide with strength of 1 wt.-% were added and the monomer solution was stirred briefly with the aid of a glass rod. Finally, 5.64 g of an aqueous solution of Bruggolite® FF6 (mixture of the disodium salt of 2-hydroxy-2-sulfinatoacetic acid, the disodium salt of 2-hydroxy-2-sulonatoacetic acid, and sodium bisulfite; available from L. Brueggemann K G, Heilbronn, Germany) with strength of 1 wt.-% was added to the monomer solution under stirring with the glass rod and the mixture polymerized by placing the glass dish with the monomer solution under a UV lamp (UV intensity=25 mW/cm$^2$) for 16 minutes. The resulting gel was ground with the aid of a commercial meat grinder (Scharfen Meat Mincer model X70G) with a 6 mm perforated disk. 5.64 g of an aqueous solution of sodium bisulfite with strength of 5 wt.-% was sprayed onto the ground gel and the gel was passed through the meat grinder two more times. The resulting gel was dried in a laboratory drying cabinet at 175° C. for 60 minutes. The product was then ground by means of an ultra-centrifugal mill (Retsch model ZM100 with 12-tooth rotor and 1.5 mm ring sieve; speed at 14000 rpm) and the sieve fraction of 150 to 600 μm was obtained by sieving of the milled product.

The resulting polymer particles had a centrifuge retention capacity (CRC) of 42.6 g/g, an content of extractables of 16.2 wt. %, and a content of residual monomers of 458 ppm.

Example 3 (Comparative)

A 2 L stainless steel vessel was initially charged with 391.1 g of 50% by weight sodium hydroxide solution and 767.6 g of deionized water. The mixture was cooled down to 15° C. by means of a cooling bath. Then 352.7 g of initially part of acrylic acid having a content of dimeric acrylic acid of 6659 ppm (acrylic acid 1) were added while stirring. The rate of addition was adjusted in such way that the temperature did not exceed 30° C. After addition, the mixture was kept at approximately 30° C. for 2 minutes. The degree of neutralization was 100 mol-%. The content of dimeric acrylic acid in the monomer solution was 104 ppm, based on acrylic acid. Thereafter, additional 117.6 g of second part of acrylic acid having a content of dimeric acrylic acid of 1973 ppm (acrylic acid 2) were added within approximately 15 minutes under stirring keeping the temperature of the mixture below 30° C. The degree of neutralization was 75 mol-%. The content of dimeric acrylic acid in the monomer solution was 244 ppm, based on acrylic acid. After addition of the second portion of acrylic acid, the mixture was cooled down to 20° C. and 1.32 g of Laromer 9015 X (ethoxylated trimethylolpropane triacrylate; available from BASF SE, Ludwigshafen, Germany) were added under stirring. Then 0.022 g of Irgacure® 651 and 0.044 g of Irgacure® 1173 were added under stirring and the mixture was cooled down to 15° C. The mixture was freed of oxygen by passing nitrogen through via a glass frit while cooling down the mixture to −0.5° C. Then the monomer solution was transferred to a glass dish. The dimensions of the glass dish were such that a layer thickness of the monomer solution of 7 cm was established. Then 7.42 g of an aqueous solution of sodium persulfate with strength of 10 wt.-% and 7.05 g of an aqueous solution of hydrogen peroxide with strength of 1 wt.-% were added and the monomer solution was stirred briefly with the aid of a glass rod. Finally, 5.64 g of an aqueous solution of Bruggolite® FF6 (mixture of the disodium salt of 2-hydroxy-2-sulfinatoacetic acid, the disodium salt of 2-hydroxy-2-sulonatoacetic acid, and sodium bisulfite; available from L. Brueggemann K G, Heilbronn, Germany) with strength of 1 wt.-% was added to the monomer solution under stirring with the glass rod and the mixture polymerized by placing the glass dish with the monomer solution under a UV lamp (UV intensity=25 mW/cm$^2$) for 16 minutes. The resulting gel was ground with the aid of a commercial meat grinder (Scharfen Meat Mincer model X70G) with a 6 mm perforated disk. 5.64 g of an aqueous solution of sodium bisulfite with strength of 5 wt.-% was sprayed onto the ground gel and the gel was passed through the meat grinder two more times. The resulting gel was dried in a laboratory drying cabinet at 175° C. for 60 minutes. The product was then ground by means of an ultra-centrifugal mill (Retsch model ZM100 with 12-tooth rotor and 1.5 mm ring sieve; speed at 14000 rpm) and the sieve fraction of 150 to 600 μm was obtained by sieving of the milled product.

The resulting polymer particles had a centrifuge retention capacity (CRC) of 42.1 g/g, an content of extractables of 17.6 wt. %, and a content of residual monomers of 780 ppm.

TABLE 1

Effect of the degree of neutralization in step (i)

| | Degree of neutralization (mol-%) | | Dimeric acrylic acid in monomer solution (ppm) | | Residual monomer in base polymer |
|---|---|---|---|---|---|
| Example | 1$^{st}$ step | 2$^{nd}$ step | 1$^{st}$ step | 2$^{nd}$ step | (ppm) |
| 1 | 110 | 75 | 0 | 344 | 485 |
| 2 | 102 | 75 | 0 | 235 | 458 |
| 3 | 100 | 75 | 104 | 244 | 780 |

Example 4 (Comparative)

Example 2 was repeated with the exemption that 345.8 g of initially part of acrylic acid having a content of dimeric acrylic acid of 6659 ppm (acrylic acid 1) was replaced by 345.8 g of initially part of acrylic acid having a content of dimeric acrylic acid of 1973 ppm, and 124.5 g of second part of acrylic acid having a content of dimeric acrylic acid of 1973 ppm (acrylic acid 2) was replaced by 124.5 g of second part of acrylic acid having a content of dimeric acrylic acid of 6659 ppm.

The content of dimeric acrylic acid in the monomer solution after addition of initially part of acrylic acid (acrylic acid 1) was 0 ppm, based on acrylic acid. The content of dimeric acrylic acid in the monomer solution after addition of second part of acrylic acid (acrylic acid 2) was 400 ppm, based on acrylic acid.

The resulting polymer particles had a centrifuge retention capacity (CRC) of 42.4 g/g, an content of extractables of 19.6 wt. %, and a content of residual monomers of 913 ppm.

TABLE 2

Effect of the dosing sequence of different acrylic acids

| Example | Content of diacrylic acid in acrylic acid (ppm) | | Dimeric acrylic acid in monomer solution (ppm) | | Residual monomer in base polymer (ppm) |
|---|---|---|---|---|---|
| | 1$^{st}$ step | 2$^{nd}$ step | 1$^{st}$ step | 2$^{nd}$ step | |
| 2 | 6659 | 1973 | 0 | 235 | 458 |
| 4 | 1973 | 6659 | 0 | 400 | 913 |

The invention claimed is:

1. A process for producing a superabsorbent, comprising polymerization of a monomer solution, comprising
   a) partly neutralized acrylic acid having a degree of neutralization from 50 to 85 mol-%,
   b) at least one crosslinker,
   c) at least one initiator,
   d) optionally one or more ethylenically unsaturated monomers copolymerizable with the acrylic acid mentioned under a) and
   e) optionally one or more water-soluble polymers,
   drying, grinding, and classifying the resulting polymer gel, optionally thermally postcrosslinking and cooling the resulting polymer particles, wherein the partly neutralized acrylic acid was prepared in a process, comprising
   i) preparing an over-neutralized acrylic acid having a degree of neutralization of at least 100.1 mol-% by mixing an acrylic acid 1 and a base, and
   ii) preparing a neutralized acrylic acid having a degree of neutralization from 50 to 85 mol-% by mixing the over-neutralized acrylic acid and an acrylic acid 2,
   wherein a content of dimeric acrylic acid in the acrylic acid 2 is lower than a content of dimeric acrylic acid in the acrylic acid 1.

2. The process according to claim 1, wherein the content of dimeric acrylic acid in the acrylic acid 2 is at least 0.1% by weight lower than the content of dimeric acrylic acid in the acrylic acid 1.

3. The process according to claim 1, wherein the content of dimeric acrylic acid in the acrylic acid 2 is at least 0.4% by weight lower than the content of dimeric acrylic acid in the acrylic acid 1.

4. The process according to claim 1, wherein the content of dimeric acrylic acid in the acrylic acid 1 is at least 0.2% by weight.

5. The process according to claim 1, wherein the content of dimeric acrylic acid in the acrylic acid 1 is at least 0.5% by weight.

6. The process according to claim 1, wherein the content of dimeric acrylic acid in the acrylic acid 2 is less than 0.5% by weight.

7. The process according to claim 1, wherein the content of dimeric acrylic acid in the acrylic acid 2 is less than 0.2% by weight.

8. The process according to claim 1, wherein degree of neutralization of the over-neutralized acrylic acid is from 101 to 106 mol-%.

9. The process according to claim 1, wherein the base is aqueous sodium hydroxide and/or aqueous potassium hydroxide.

10. The process according to claim 1, wherein the superabsorbent has a centrifuge retention capacity of at least 15 g/g.

11. The process according to claim 1, wherein a temperature of the acrylic acid 1 and/or a temperature of the acrylic acid 2 is in a range from 15 to 25° C.

12. The process according to claim 1, wherein the acrylic acid having a lower content of dimeric acrylic acid than the acrylic acid 2 is used as a new acrylic acid 2 and the former acrylic acid 2 is combined with the former acrylic acid 1 forming a new acrylic acid 1.

* * * * *